US007208287B2

(12) United States Patent
Kishi et al.

(10) Patent No.: US 7,208,287 B2
(45) Date of Patent: Apr. 24, 2007

(54) REAGENT SET AND METHOD FOR DETECTING CHOLESTEROL IN A HIGH-DENSITY LIPOPROTEIN OR LOW DENSITY LIPOPROTEIN

(75) Inventors: Koji Kishi, Kobe (JP); Tsutomu Kakuyama, Kobe (JP); Koji Ochiai, Kobe (JP); Yuzo Hasegawa, Kobe (JP)

(73) Assignee: Sysmex Corporation, Hyogo (JP)

( * ) Notice: Subject to any disclaimer, the term of this patent is extended or adjusted under 35 U.S.C. 154(b) by 86 days.

(21) Appl. No.: 10/776,970

(22) Filed: Feb. 11, 2004

(65) Prior Publication Data
US 2004/0161811 A1  Aug. 19, 2004

Related U.S. Application Data

(62) Division of application No. 09/914,552, filed as application No. PCT/JP00/01172 on Feb. 29, 2000, now abandoned.

(30) Foreign Application Priority Data

Mar. 1, 1999  (JP) .................................. 11-53330

(51) Int. Cl.
*C12Q 1/60* (2006.01)
(52) U.S. Cl. ......................................... 435/11; 435/175
(58) Field of Classification Search .................. 435/11, 435/19, 25, 26, 175, 810, 975; 436/16, 17, 436/71
See application file for complete search history.

(56) References Cited

U.S. PATENT DOCUMENTS

| | | | | |
|---|---|---|---|---|
| 4,892,815 | A | | 1/1990 | Kersher et al. ................. 435/7 |
| 4,892,816 | A | | 1/1990 | Akiba et al. .................... 435/11 |
| 5,185,247 | A | * | 2/1993 | Ismail et al. ................... 435/14 |
| 5,460,974 | A | * | 10/1995 | Kozak et al. ................. 436/71 |
| 5,814,472 | A | | 9/1998 | Miki et al. ..................... 435/11 |
| 5,925,534 | A | | 7/1999 | Miki et al. ..................... 435/11 |
| 6,057,118 | A | * | 5/2000 | Nakamura et al. ............ 435/11 |
| 6,114,134 | A | * | 9/2000 | Kishi et al. .................... 435/11 |
| 6,333,166 | B1 | * | 12/2001 | Nakamura et al. ............ 435/11 |

FOREIGN PATENT DOCUMENTS

| | | | |
|---|---|---|---|
| EP | 0887422 | | 12/1998 |
| EP | 0913484 | | 5/1999 |
| EP | 1020532 | | 7/2000 |
| JP | 09-000299 | | 1/1997 |
| JP | 11-18798 | * | 7/1997 |
| JP | 9-285298 | * | 11/1997 |
| JP | 10-311833 | | 11/1998 |
| JP | 11-56395 | | 3/1999 |
| JP | 11-155595 | * | 11/1999 |
| JP | 5-176797 | * | 12/1999 |
| JP | 2000-325097 | * | 11/2000 |
| WO | WO 97/45553 | | 12/1997 |
| WO | WO 98/59068 | | 12/1998 |

OTHER PUBLICATIONS

Supplementary Partial European Search Report dated Jun. 27, 2002.
Gedik N. Direct Measurement of HDL Cholesterol in Serum . . . Biyokimya Dergisi 23(1) Mar. 10-17, 1998.
Yamauchi K. Evaluation of Reactivity Using Direct Assay Methods for HDL Lipoprotein Cholesterol. Rinsho Kagaku 1197.26(3) 150-156, no date given.
Sugiuchi H. Homogeneous Assay for Measuring LDL Cholesterol . . . Clinical Chemistry 44(3)522-531, 1998.
International Preliminary Examination Report dated Dec. 21, 2001.

* cited by examiner

*Primary Examiner*—Ralph Gitomer
(74) *Attorney, Agent, or Firm*—Kilyk & Bowersox, P.L.L.C.

(57) ABSTRACT

A method for quantitating a specific component in lipoproteins contained in a biological sample, for example, HDL (high-density lipoprotein), LDL (low-density lipoprotein) or VLDL (very low-density lipoprotein) by using a commonly employed automatic analyzer without centrifuging or making the reaction liquor cloudy due to complexes or aggregates. Namely, a controlling means, whereby an enzyme reaction can be carried out exclusively for the target component, is introduced into a method for enzymatically assaying a component in a specific lipoprotein fraction in the serum, thereby specifically assaying the component.

19 Claims, 4 Drawing Sheets

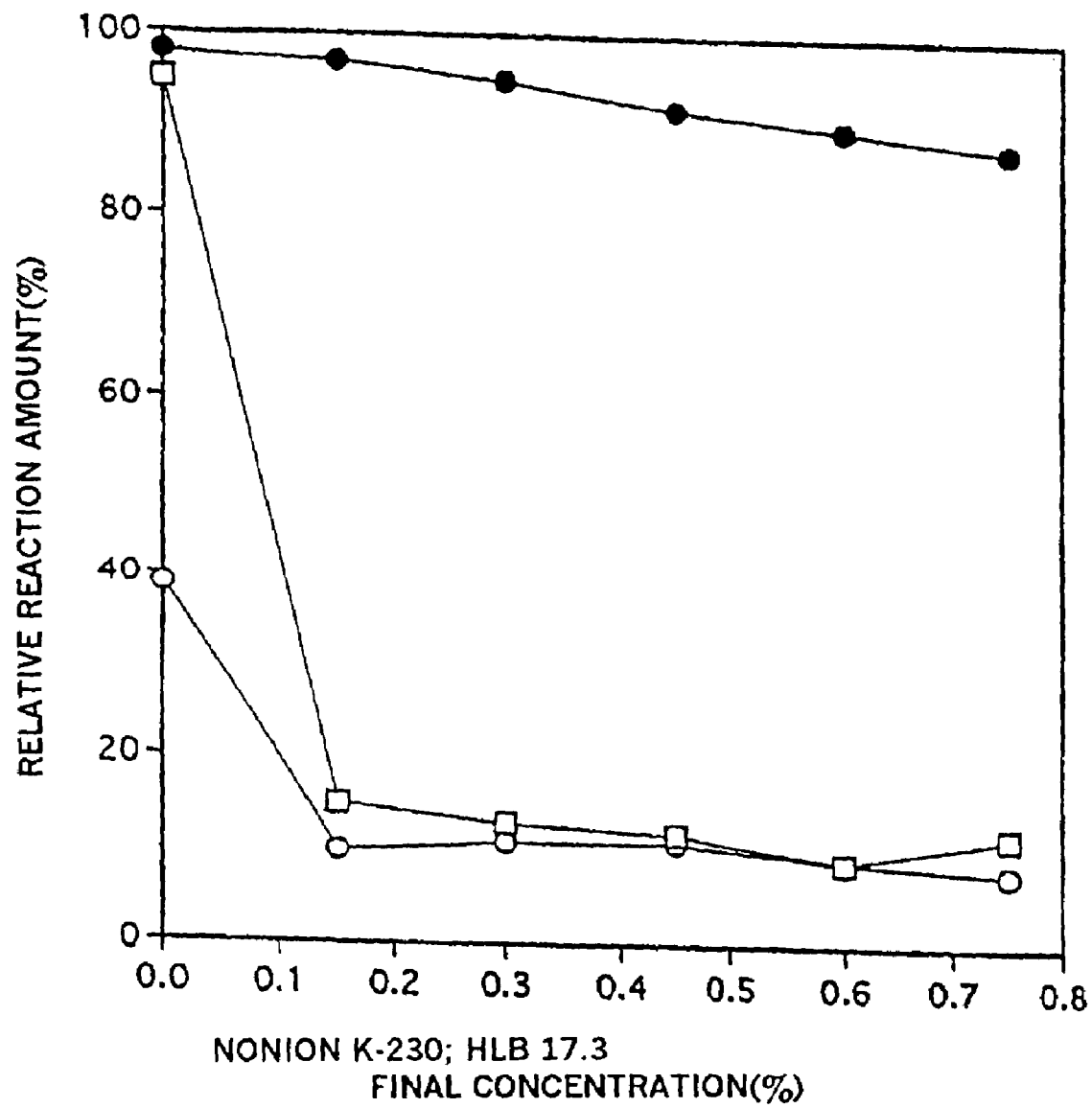

REAGENT SET AND METHOD FOR DETECTING CHOLESTEROL IN A HIGH-DENSITY LIPOPROTEIN OR LOW DENSITY LIPOPROTEIN

This application is a divisional patent application of U.S. patent application Ser. No. 09/914,552 filed Aug. 30, 2001, now abandoned which is a National Phase entry filed under Rule 371 of International Patent Application No. PCT/JP00/01172 filed Feb. 29, 2000.

FIELD OF THE INVENTION

The present invention relates to assaying means and an assaying method for a specific component in a lipoprotein fraction in the serum by an enzymatic reaction.

BACKGROUND OF THE INVENTION

From old times, a lipoprotein has been fractionated into high-densitylipoprotein (HDL), low-densitylipoprotein (LDL), very low-density lipoprotein (VLDL), and chylomicron (CM) by an ultracentrifuge operation. Said operation needs skillfulness. After the installation of an ultracentrifuge, a centrifuge is required for over several days. For this reason, many specimens cannot be treated in short time.

Alternatively, a method for mixing the serum with a solution, in which polyethylene glycol or polyanion, such as dextran sulfate and a divalent cation, including magnesium, calcium and etc., are coexisted or a solution in which phosphotungstic acid and a divalent cation are coexisted to precipitate LDL, VLDL and CM, and fractionated only HDL that remains in the supernatant after the centrifuge has become predominant.

The method may be carried out by applying an automatic analyzer that has been widely spread in a field of clinical tests. That is, a concentration of the cholesterol in the fractionated HDL may be determined by utilizing an enzymatic method for assaying the total cholesterol using an automatic analyzer that has already been established. However, said method also needs a centrifuge operation, which is performed at a low speed, and when mixing the fractionating agent with the serum problems such as artificial quantitation error and confusion of specimens have occurred. In addition, the assay could not be performed simultaneously with the assay of other general biological items. The clinical tests need to be responded quickly and has been demanded to simultaneously assay one test item together with other test items so as to be shorten a time for tests.

On the other hand, there has also been a report that laid importance on the cholesterol value in LDL, which is a clinical risk factor for arteriosclerosis (Standard Value of Total Cholesterol and Reason for Setting thereof; Arteriosclerosis 24(6), 280 (1996)). Currently, the cholesterol value in LDL is obtained from the results for measurements of total cholesterol (T-CHO), neutral fat (TG) and cholesterol in HDL, by introducing an empirical factor in equation. An equation [Friedewald, W. T., et al., Clin. Chem., 18, 499–502 (1972)] is as follows:

Cholesterol value in LDL=Total cholesterol value−
HDL cholesterol value−TG value/5.

Said method can not be established unless all the three items to be assayed are accurately obtained. Further, reportedly, the TG value of exceeding 400 mg/dL or the cholesterol concentration in LDL of 100 mg/dL or less leads to a failure such that the calculated value does not reflect the cholesterol concentration in LDL (Warnick, G. R., et al., Clin. Chem., 36(1), 15–19 (1990)), (McNamara, J. R., et al., Clin. Chem., 36(1), 36–42 (1990)). Therefore, it has been difficult to detect extraordinary values of cholesterol in LDL which is the object of the assay by this method.

Besides, there has been a method of separating lipoprotein by electrophoresis and measuring the amount of the proteins and a method of assaying the cholesterol in individual lipoprotein by HPLC. The both methods have poor specimen treating capability and need an expensive dedicated apparatus.

Recently, in order to solve the above-mentioned problems in relation to the assay of the cholesterol in HDL, a kit for automatically assaying the cholesterol in HDL has been developed and widely spread. The technologies disclosed in U.S. Pat. No. 2,600,065, Laid-open Japanese Patent Publication No. Hei 8-201393 and Laid-open Japanese Patent publication No. Hei 8-131195 use a fractionating agent in combination and a metal contained in the fractionating agent as a divalent cation forms insoluble precipitates with a detergent, generally used in the automatic analyzer, and the precipitates accumulate in a waste liquor disposal mechanism in the apparatus and results in causing breakdown.

Further, during the assay reaction, insoluble aggregates are formed to cause turbidity that will affect on the data of assay and not only the turbidity causes measurement errors but also the aggregates contaminate a reaction cell, to thereby give not a little influence on the results of the assay on other biochemical items being simultaneously assayed.

The automatic method for assaying cholesterol in HDL may apply known photometry that may be selected from 2-points end method, a rate method, a double rate method, a fix time method and the like, so that the assay can be performed in a turbid state. However, even with these photometric methods, the assay in the turbid state causes a problem on accuracy of assay when a certain change in turbidity is caused during the reaction. If a reaction solution is turbid, the reproducibility becomes decrease. Therefore, limitation is posed on specimens to be assayed, wide assay wavelength ranges cannot be used, or specimens from various patients cannot be served. For example, a disadvantage may be appeared that at around 340 nm (in short wavelength range), the absorbance becomes 2 to 3 or more due to the turbidity phenomenon by the aggregates, thereby often exceeding over the allowable range in the analyzer.

The technology disclosed in Laid-open Japanese Patent Publication No. Hei 9-96637 that never use divalent cation, is a method by adding lipoprotein and an antiserum agglutinating therewith. Said method also forms antigen antibody aggregates that will cause the turbidity, resulting in the contamination of the reaction cell. Therefore, the aggregates contaminate the reaction cell, to thereby give not a little influence on data of the assay in other biochemical items being simultaneously assayed. Further, since the turbidity in the reaction solution increases, an accurate assay of the cholesterol in HDL particularly by photometry in a short wavelength region for the same reason as mentioned above.

These technologies are made up of contriving a common technology of preventing enzymatic reactions and a photometry by forming complexes or aggregates and the adverse influence that the turbidity inherently has, cannot be solved. The technology that finally eliminates such turbidity includes one of countermeasures for turbidity. As disclosed in Laid-open Japanese Patent Publication No. Hei 6-242110, addition of the operation for finally eliminating turbidity may give rise to accurate measured data. However, this method requires at least 3 or 4 steps of divided reagent dispensing operation. Although the commercially available automatic analyzers include those that can cope with a 3 or 4-step of divided reagent dispensing operation, generally prevailing automatic analyzers for biochemical items mostly cope with at most 2-step reagent dispensing operation, so that the method could not be applied in a certain case.

On the other hand, the assay of the cholesterol in LDL is in such a position that the above-mentioned calculation method must be used even at present. Recentry, methods for assaying the cholesterol in LDL addressed to full automation has been reported such technologies as disclosed in Laid-open Japanese Patent Publication No. Hei 07-280812, WO96/29599, and Laid-open Japanese Patent publication No. Hei 09-313200. These techniques reside in the extension of the technology which involves formation of aggregates or complexes, thus, the control of turbidity upon the assay is a problem to be solved in future.

SUMMARY OF THE INVENTION

An object of the present invention is to provide a method for assaying a specific component in a lipoprotein fraction in the serum by an enzymatic reaction, which comprises quantitating a component in lipoprotein contained in a biological sample, such as, HDL (high-density lipoprotein), LDL (low-density lipoprotein), VLDL (very low-density lipoprotein) and the like, by using a commonly employed automatic analyzer without centrifuging operation or forming turbid in the reaction solution due to complexes or aggregates upon the treatment.

The present invention provides a method for assaying a component in a specific lipoprotein fraction in a serum by an enzymatic reaction, comprising introducing a means for controlling the reactivity of an enzyme acting on a component in the lipoprotein fraction, thereby specifically assaying the component. The means for controlling the reactivity of the enzyme acting on the specific component in the lipoprotein fraction includes adding a substance that controls the ion strength of the enzymatic reaction solution, selecting a nonionic surfactant, and/or using a selected enzyme having reaction specificity to the specific lipoprotein.

The present invention provides a method for assaying a component in HDL, a method for assaying a component in LDL, and/or a method for assaying a component in VLDL, by appropriately selecting the above three means and utilizing singly or in combination.

The assaying method of the present invention, in the case where a component in the high-density lipoprotein (HDL) is to be assayed is characterized by introducing therein sufficiently increasing the ion strength of the reaction solution, and/or activating lipoprotein lipase and/or cholesterol esterase that acts preferentially on HDL, and/or using a nonionic surfactant that has reaction selectivity to HDL and has an HLB value of 16 or more.

Further, the assaying method of the present invention in the case where the cholesterol in low-density lipoprotein (LDL) is to be assayed, provides a method comprising at first selectively subjecting a cholesterol component in an HDL fraction to an enzymatic reaction to assay or digest thereof in a first enzymatic reaction system, and then assaying the cholesterol component in the LDL fraction by an enzymatic reaction by utilizing a nonionic surfactant that has an HLB value of 11 to 13 in a second enzymatic reaction system.

Furthermore, the assaying method of the present invention provides a method comprising simultaneously or separately treating a first enzyme system and second enzyme system to have the cholesterol component in a very low-density lipoprotein (VLDL) fraction remained, and then introducing a means for decomposing the VLDL fraction to assay the cholesterol component in the VLDL fraction by an enzymatic reaction. The cholesterol in the VLDL fraction may be assayed without accompanying elimination of HDL and LDL.

The assaying method of the present invention also includes an assaying method further comprising a step for adding cholesterol oxidase or cholesterol dehydrogenase to the above-mentioned assaying method of the present invention to digest free cholesterol.

The assaying method of the present invention described above is characterized in that the pH of the enzymatic reaction solution is within such a range that the lipoprotein does not cause agglutination nor make the reaction solution cloudy and is selected in view of an optimum pH of the enzyme that catalyzes the enzymatic reaction of the component in the lipoprotein.

BRIEF DESCRIPTION OF THE DRAWINGS

FIG. 4 is a diagram illustrating the effect of addition of an ion strength controlling substance for enzymatic reaction solution, nonionic surfactant NONION K-230, and selected enzyme. (Experiment 4) In the figure, -●- indicates the relative reaction amount (%) of an HDL fraction, -○- indicates the relative reaction amount (%) of an LDL fraction, and -□- indicates the relative reaction amount (%) of a VLDL fraction.

DETAILED DESCRIPTION OF A PREFERRED EMBODIMENT OF THE INVENTION

Figure 1:
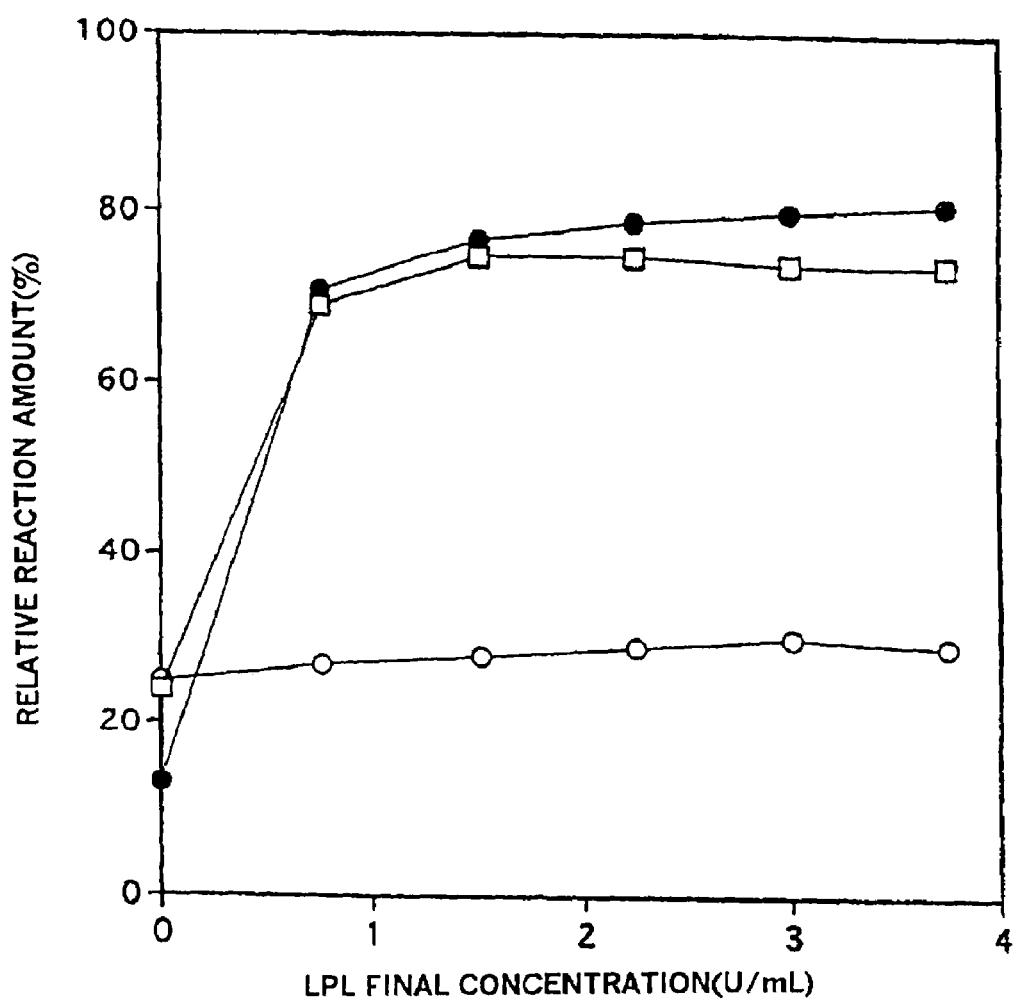
FIG. 1 is a diagram illustrating the effect of addition of lipoprotein lipase (LPL; derived from Chromobacterium viscosum). (Experiment 1) In the figure, -●- indicates the relative reaction amount (%) of an HDL fraction, -○- indicates the relative reaction amount (%) of an LDL fraction, and -□- indicates the relative reaction amount (%) of a VLDL fraction.

Controlling the reactivity of an enzyme on a specific lipoprotein component by addition of an ion strength controlling substance for an enzymatic reaction solution according to the present invention, means dissolving a specific lipoprotein fraction by utilizing the property that respective lipoprotein fractions, namely, HDL, LDL and VLDL, have different water solubilities and selectively carrying out the enzymatic reaction with a component in the specific fraction. As one means for achieving the object, the ion strength of a specimen is elevated. The ion strength for selectively dissolving HDL can be obtained by adding, for example, a hydrazine in a concentration of about 30 mM, preferably 60 mM or more. As the hydrazine, hydrazine groups as well as salts, hydrates and solvates thereof, that are selected to be used based on the selective solubility of HDL as an index. Similarly, NaCl, urea, guanidines, semicarbazides, and the like may also be used. The compounds which proceeds the ion strength may be used singly or a plurality in combination. The applicable concentration of these compound can be determined by repeated experiments when in use based on the selective solubility of HDL as an index.

In the present invention, the means for directly and/or preferentially enabling an enzymatic reaction, with respect to a component in a specific lipoprotein fraction in the reaction solution by utilizing the reaction specificity of an enzyme to a specific lipoprotein is carried out by selecting a lipoprotein lipase (LPL) and/or cholesterol esterase (CE) that preferentially act(s) on the HDL fraction. The enzyme includes commercially available LPL and CE, derived from Chromobacterium viscosum. In the case where an LDL fraction is aimed, enzymes derived from the genus Pseudomonas and the like, may be appropriately selected. The enzymes may be or do not have to be subject to various modifications as far as the enzyme activity and selectivity to the specific lipoprotein fraction are maintained. An addition amount of the enzyme is increased or decreased and controlled depending on the amount of a substrate known per se.

In the present invention, the means for directly and/or preferentially enabling an enzymatic reaction with respect to a component in a specific lipoprotein fraction in the reaction solution by utilizing the reaction selectivity of a selected nonionic surfactant to the specific lipoprotein can be identified by the HLB value of the nonionic surfactant.

In the case where an HDL fraction is aimed, one having the HLB value of 16 or more, preferably 17 or more, is selected. More preferably, polyoxyethylene ethers having the HLB value of 17 or more are selected. The selected surfactants inhibit the enzymatic action of LPL, CE, cholesterol dehydrogenase (CDH) or the like on the LDL fraction and VLDL fraction. Specific examples thereof will be listed below. A nonionic surfactant used in the present invention can be optionally selected using HLB value as an index and is not limited to the following examples: cetyl ether (C16) (hexadecyl ether) (tradename: Nikko Chemical Co., Ltd.: BC-25TX, BC-30TX, BC-40TX), lauryl ether (C12) (dodecyl ether) (tradename: Nikko Chemical Co., Ltd.: BL-21, BL-25), oleyl ether (trade name: Nikko Chemical Co., Ltd.: BO-50), behenyl ether (C22) (tradename: Nikko Chemical Co., Ltd.: BB-30), polyoxyethylene lauryl ether (tradename: Nippon Oils & Fats Co., Ltd.: Nonion K-230), polyoxyethylene Monolaurate (tradename: Nippon Oils & Fats Co., Ltd.: Nonion S-40), polyoxyethylene ethers (tradename: Sigma: Brij 98, Brij 721, Brij 78, Brij 99) and the like.

In the case where an LDL fraction or a VLDL fraction is aimed, in particular in the case where the enzymatic reaction with a component in the LDL fraction is positively aimed, a nonionic surfactant having an HLB value of 11 to 13 is selected. Example may be made of Triton X-100, Nonion HS210, and Nonion A-10R (Nippon Oils & Fats Co., Ltd.). However, the surfactant used for assaying a component in the LDL fraction may also be optionally selected using HLB value as an index and is not limited to these thereto.

The addition amount of the above-mentioned surfactant may vary depending on the amount of lipoprotein to be assayed. The amount shown in the case where the HDL and LDL are aimed, is about 180 μL of a reagent having a surfactant concentration of 0.01 to 10% per about 5 μL of a specimen. With such amount of the surfactant, the HDL or LDL is selectively decomposed to enable the enzymatic reaction of a component contained therein. In the case where a VLDL is aimed, the surfactant is used after adjusting a concentration to 0.05 to 20%. Thus, the VLDL is selectively decomposed to enable the enzymatic reaction of a component contained therein.

The pH of the reaction solution, in which enzymatic reaction occurs, is within such a range that lipoprotein does not cause agglutination nor makes the reaction solution cloudy and is selected taking the optimal pH of the enzyme that acts on the component in the lipoprotein. Preferably, the pH is about 6 to about 9. If the pH is about 6 or less, the lipoprotein makes the reaction solution cloudy. Although the pH around 7, at which the lipoprotein is relatively stable, may be selected for controlling the assaying conditions, the optimal pHs of the enzymes such as COD (cholesterol oxidase), CDH (cholesterol dehydrogenase), LPL, CE, and the like are also taken into consideration. Preferably, the reactions of CDH, LPL, and CE are at the pH of about 7 to about 9, and the reaction of COD is at the pH of about 6 to about 8. The reaction solution is preferably adjusted with a buffer solution and various buffer solutions usually used in biochemical reactions may be used. Examples thereof include a HEPES (2-[4-(2-hydroxyethyl)-1-piperazinyl] ethanesulfonicacid) buffer solution, a PIPES (piperazine-1, 4'-bis(2-ethanesulfonic acid)) buffer solution, a TAPS (N-Tris-(hydroxymethyl)-methyl-3-aminopropanesulfonic acid) buffer solution, a BES-BisTris buffer solution, a Tris-hydrochloride buffer solution, a 3-morpholinopropane-sulfonate (MOPS) buffer solution, and a phosphate buffer solution. The buffer solution are optionally selected depending on the compatibility with the additives before using thereof. In the examples and experiment examples of the present invention, PIPES buffer solution and TAPS buffer solution were respectively used according to a pH condition.

If desired, free cholesterol in the LDL, VLDL and chylomicron may be preliminarily reacted with COD or CDH to convert into cholestenone hydrazone in the presence of hydrazine, to make a non-substrate state for the time when assaying the cholesterol in HDL because the free cholesterol could participate in the reaction upon assaying the cholesterol in HDL to frequently cause errors. The technology for converting the free cholesterol into a non-substrate is well known and reference may be made to Laid-open Japanese Patent Publication Laid-open No. Hei 5-176797, for example.

In the present invention, the above-mentioned three means, i.e., selection of ion strength, selection of enzyme, and selection of surfactant are introduced singly or in optional combinations. More preferably, all of the means are introduced simultaneously. However, it is not always necessary that all means are introduced simultaneously.

In the case where the cholesterol component in the HDL is to be assayed, a first requirement is to control the ion strength to a sufficiently high level so that a component in the high-density lipoprotein (HDL) having high water solubility can be readily dissolved in the solution. A second requirement is to select lipoprotein lipase (LPL) and/or cholesterol esterase (CE) that preferentially act(s) on the HDL fraction and allow to react therewith. A third requirement is to use a nonionic surfactant that has reaction selectivity for the HDL fraction and having the HLB value of 16 or more and carry out the enzymatic reaction directly or preferentially on a component in the HDL fraction in the reaction solution.

In the case where cholesterol as a component in the lipoprotein by an enzymatic assaying method when CDH is used as the enzyme, β-nicotinamide adenine dinucleotide of the oxide type (NAD), thionicotinamide adenine dinucleotide of the oxide type (t-NAD), β-nicotinamide adenine dinucleotide phosphate of the oxide type (NADP), thionicotinamide adenine dinucleotide phosphate of the oxide type (t-NADP) or the like is used. When COD is used, assay is performed by using a peroxidase (POD) and a known hydrogen peroxide quantitation method in combination. The concentrations of cholic acids as an activator for enzyme and of surfactants that are required for the assay of the total cholesterol may be controlled by optionally selecting the conditions and repeating experiments.

In the case where the cholesterol component in the LDL is to be assayed, first the cholesterol component in the above-mentioned HDL fraction is selectively subject to an enzymatic reaction in a first enzymatic reaction system and then LPL and/or CE that act(s) on the LDL fraction and a surfactant that positively decomposes LDL are added to thereby detect the reaction product by CDH.

The assay of the enzymatic reaction product is performed by optionally selecting an assay system as shown below from the well-known methods, for quantitating cholesterol that is a compound generated by the enzymatic action of CE, LPL or the like. For example, in the case where a CDH-NAD system is used, the absorbance at 340 nm is measured. In the case where a CDH-t-NAD system is used, the absorbance at 405 nm is measured. In the case where a COD system is used, the absorbance at 500 nm or more (depending on the type of chromogen) is measured. As the photometry, a rate method, a 2-point end method or the like that is already known may be used as desired.

The method for assaying a specific component in the lipoprotein fraction introduced by appropriately selecting means of the present invention singly or in combination do not make turbid in the reaction solution due to complexes or aggregates that will be formed in the reaction liquor. Thus, a precision in assay for the specific object cholesterol in lipoprotein can be increased.

Further, use of the assaying method of the present invention enables to perform assay of the cholesterol in lipoprotein and assay of biochemical test items simultaneously, since simultaneous assay of the biochemical test items will not adversely affect the assay results. Furthermore, the assaying method of the present invention does not need centrifugation and uses a 2-step reagent dispensing operation so that it can be applied to most of the automatic analyzers commonly used, and simplification of the assay can be achieved.

Still further, the present invention can be applied to the assay for not only the cholesterol in lipoprotein but also for other lipid components (neutral fats, phospholipids, etc.). The present invention is disclosed in more detailed by way of examples, which are not construed to limit thereof. In the example, part and percent show based on weight unless otherwise specified.

EXAMPLES

Example 1

The following reagents were prepared. As specimens serum 10 sampled from ordinary people were used. The assays were practiced on a Hitachi 7170 Type automatic analyzer. The operational method was as follows. First, to 5 μL of each specimen was added with 180 μL of reagent 1-A, -B or -C, and kept in a constant temperature at 37° C. for 5 minutes. At this point of time, absorbance 1 was measured at a main wavelength of 340 nm and a side wavelength of 570 nm, respectively. Furthermore, 60 μL of reagent 2 was added, and kept in a constant temperature at 37° C. for 5 minutes. At this point of time, absorbance 2 was measured at a main wavelength of 340 nm and a side wavelength of 570 nm, respectively. A difference between the absorbances 1 and 2 was obtained and the value of each specimen was converted using a control, whose HDL-cholesterol concentration was already known, as a standard solution. As a control method, a polyethylene glycol (PG) method was used. In the PG method, PG pole produced by International Reagents Co., Ltd. was used. Further, the cholesterol concentration of the supernatant after the centrifuge was obtained using T-CHO reagent A produced by International Reagents Co., Ltd. As results of the assay, comparisons with the control method were shown in Table 1. The assays using reagents 1-A, 1-B and 1-C gave satisfactory results that well coincided with those obtained by the control method.

| Reagent 1-A | |
| --- | --- |
| Buffer solution | pH 7.0 |
| Hydrazinium dichloride | 100 mmol/L |
| β-NAD | 6.0 mmol/L |
| Sodium cholate | 0.1% |
| Nonion K-230 (HLB value 17.3) | 0.6% |
| Reagent 1-B | |
| Buffer solution | pH 7.0 |
| Hydrazinium dichloride | 100 mmol/L |
| β-NAD | 6.0 mmol/L |
| Brij 97 (HLB value 19) | 0.24% |
| Sodium cholate | 0.1% |
| Reagent 1-C | |
| Buffer solution | pH 7.0 |
| Hydrazinium dichloride | 100 mmol/L |
| β-NAD | 6.0 mmol/L |
| Nonion K-230 (HLB value 17.3) | 0.2% |
| Cholesterol oxidase (COD) | 1.0 U/mL |
| Sodium cholate | 0.1% |
| Reagent 2 | |
| Buffer solution | pH 8.5 |
| Cholesterol dehydrogenase (CDH) | 20.0 U/mL |
| LPL (derived from *Chromobacterium viscosum*) | 6.0 U/mL |
| Sodium cholate | 0.2% |

TABLE 1

| Specimen | Control Method | Reagent 1-A | Reagent 1-B | Reagent 1-C |
| --- | --- | --- | --- | --- |
| 1 | 31.6 | 33.1 | 22.6 | 34.0 |
| 2 | 71.6 | 71.3 | 70.8 | 70.3 |
| 3 | 53.8 | 58.8 | 56.3 | 58.2 |
| 4 | 42.4 | 46.3 | 39.8 | 45.2 |
| 8 | 52.6 | 54.8 | 49.2 | 56.2 |
| 9 | 35.9 | 43.3 | 39.5 | 42.4 |
| 7 | 41.1 | 44.0 | 41.2 | 44.9 |
| 8 | 26.0 | 28.2 | 27.6 | 27.3 |
| 9 | 60.0 | 67.9 | 66.9 | 61.0 |
| 10 | 112.0 | 119.6 | 121.1 | 119.7 |
| Correlation | | 0.995 | 0.989 | 0.995 |
| Inclination of regression curve | | 1.039 | 1.123 | 1.031 |
| Intercept of regression curve | | 1.968 | −5.695 | 1.569 |

Unit: mg/dL

Example 2

The following reagents were prepared. As specimens serum 10 sampled from ordinary person were used. The assays were practiced on a Hitachi 7170 Type automatic analyzer. The operational method was as follows. First, to 3 μL of each specimen was added with 210 μL of reagent A-1, and kept in a constant temperature at 37° C. for 5 minutes. At this point of time, absorbance 1 was measured at a main wavelength of 340 nm and a side wavelength of 570 nm, respectively. Furthermore, 70 μL of reagent A-2 was added, and kept in a constant temperature at 37° C. for 5 minutes. At this point of time, absorbance 2 was measured at a main wavelength of 340 nm and a side wavelength of 570 nm, respectively. A difference between the absorbances 1 and 2 was obtained and the value of each specimen was converted using a control, whose HDL-cholesterol concentration was already known, as a standard solution. Reagents B-1 and B-2 were used in the same manner as above. The values by the control method were obtained in accordance with the Friedewald equation. The HDL cholesterol values were obtained using PG pole produced by International Reagents Co., Ltd. The total cholesterol values were obtained using T-CHO reagent A that was produced by International Reagents Co., Ltd. The TG values were obtained using TG reagent A that was produced by International Reagents Co., Ltd. The results obtained are shown in Table 2. The method of the example gave satisfactory results as compared with the control method.

Reagent A-1

| | |
|---|---|
| Buffer solution | pH 7.8 |
| Hydrazinium dichloride | 100 mmol/L |
| Cholesterol dehydrogenase (CDH) | 20.0 U/mL |
| β-NAD | 6.0 mmol/L |
| LPL (derived from *Chromobacterium viscosum*) | 6.0 U/mL |
| Nonion K-230 (HLB value 17.3) | 0.15% |
| Sodium cholate | 0.1% |

Reagent A-2

| | |
|---|---|
| Buffer solution | pH 8.5 |
| CE (derived from Pseudomonas) | 3.0 U/mL |
| Nonion A-10R | 0.5% |
| Sodium deoxycholate | 8.0 mmol/L |

Reagent B-1

| | |
|---|---|
| Buffer solution | pH 7.8 |
| Hydrazinium dichloride | 100 mmol/L |
| β-NAD | 5.0 mmol/L |
| Cholesterol oxidase (COD) | 0.3 U/mL |
| LPL (derived from *Chromobacterium viscosum*) | 6.0 U/mL |
| Nonion K-230 (HLB value 17.3) | 0.15% |
| Sodium cholate | 0.1% |

Reagent B-2

| | |
|---|---|
| Buffer solution | pH 8.5 |
| Cholesterol dehydrogenase (CDH) | 20.0 U/mL |
| CE (derived from Pseudomonas) | 3.0 U/mL |
| Nonion A-10R | 0.5% |
| Sodium deoxycholate | 8.0 mmol/L |

TABLE 2

| Specimen | Control Method | Reagent A | Reagent B |
|---|---|---|---|
| 1 | 151 | 155 | 147 |
| 2 | 173 | 188 | 168 |
| 3 | 236 | 234 | 220 |
| 4 | 79 | 79 | 66 |
| 8 | 173 | 167 | 157 |
| 9 | 170 | 173 | 163 |
| 7 | 118 | 123 | 111 |
| 8 | 87 | 93 | 81 |
| 9 | 92 | 95 | 90 |
| 10 | 64 | 72 | 64 |
| Correlation | | 0.995 | 0.996 |
| Inclination of regression curve | | 0.973 | 0.943 |
| Intercept of regression curve | | 7.235 | 0.083 |

Unit: mg/dL

Example 3

Experiment Examples

The following reagents were prepared and the effects of each factor were studied in Experiments 1 to 4. As specimens, HDL, LDL and VLDL fractions were used, which were obtained by pooling serum 10, sampled from ordinary person, and followed by ultracentrifuge. The assays were practiced on a Hitachi 7170 Type automatic analyzer. The operation method was as follows. First, to 5 μL of each specimen was added with 180 μL of reagent 1-D, -E, -F, or -G, and kept in a constant temperature at 37° C. for 5 minutes. At this point of time, absorbance 1 was measured at a main wavelength of 340 nm and a side wavelength of 570 nm, respectively. Furthermore, 60 μL of reagent 2-D, -E, -F or -G corresponding to reagent 1-D, -E, -F, or -G, respectively, was added, and kept in a constant temperature at 37° C. for 5 minutes. At this point of time, absorbance 2 was measured at a main wavelength of 340 nm and a side wavelength of 570 nm, respectively. A difference between the absorbances 1 and 2 was obtained.

Reagent 1-D and Reagent 2-D for Experiment 1

Reagent 1-D

| | |
|---|---|
| Buffer solution | pH 7.0 |
| β-NAD | 6.0 mmol/L |
| Sodium cholate | 0.1% |

Reagent 2-D

| | |
|---|---|
| Buffer solution | pH 8.5 |
| Cholesterol dehydrogenase (CDH) | 20.0 U/mL |
| LPL (derived from *Chromobacterium viscosum*) | 0 to 15 U/mL |
| Sodium cholate | 0.2% |

Reagent 1-E and Reagent 2-E for Experiment 2

Reagent 1-E

| | |
|---|---|
| Buffer solution | pH 7.0 |
| Hydrazinium dichloride | 0 to 100 mmol/L |
| β-NAD | 6.0 mmol/L |
| Sodium cholate | 0.1% |

Reagent 2-E

| | |
|---|---|
| Buffer solution | pH 8.5 |
| Cholesterol dehydrogenase (CDH) | 20.0 U/mL |
| LPL (derived from *Chromobacterium viscosum*) | 6.0 U/mL |
| Sodium cholate | 0.2% |

-continued

Reagent 1-F and Reagent 2-F for Experiment 3

Reagent 1-F

| | |
|---|---|
| Buffer solution | pH 7.0 |
| β-NAD | 6.0 mmol/L |
| Nonion K-230 (HLB value 17.3) | 0 to 1.0% |
| Sodium cholate | 0.1% |

Reagent 2-F

| | |
|---|---|
| Buffer solution | pH 8.5 |
| Cholesterol dehydrogenase (CDH) | 20.0 U/mL |
| LPL (derived from *Chromobacterium viscosum*) | 6.0 U/mL |
| Sodium cholate | 0.2% |

Reagent 1-G and Reagent 2-G for Experiment 4

Reagent 1-G

| | |
|---|---|
| Buffer solution | pH 7.0 |
| Hydrazinium dichloride | 100 mmol/L |
| β-NAD | 6.0 mmol/L |
| Nonion K-230 (HLB value 17.3) | 0 to 1.0% |
| Sodium cholate | 0.1% |

Reagent 2-G

| | |
|---|---|
| Buffer solution | pH 8.5 |
| Cholesterol dehydrogenase (CDH) | 20.0 U/mL |
| LPL (derived from *Chromobacterium viscosum*) | 6.0 U/mL |
| Sodium cholate | 0.2% |

Discussion on Experiment 1 (FIG. 1)

The results of examination on the specificity of LPL derived from Chromobacterium viscosum to the lipoprotein fraction indicated that LPL acted very strongly on the HDL and VLDL fractions and showed weak reactivity with respect to the LDL fraction. Using this enzyme, the following experiments were proceeded. Note that, in each reagent, 6 U/mL of the enzyme was added.

Figure 2:
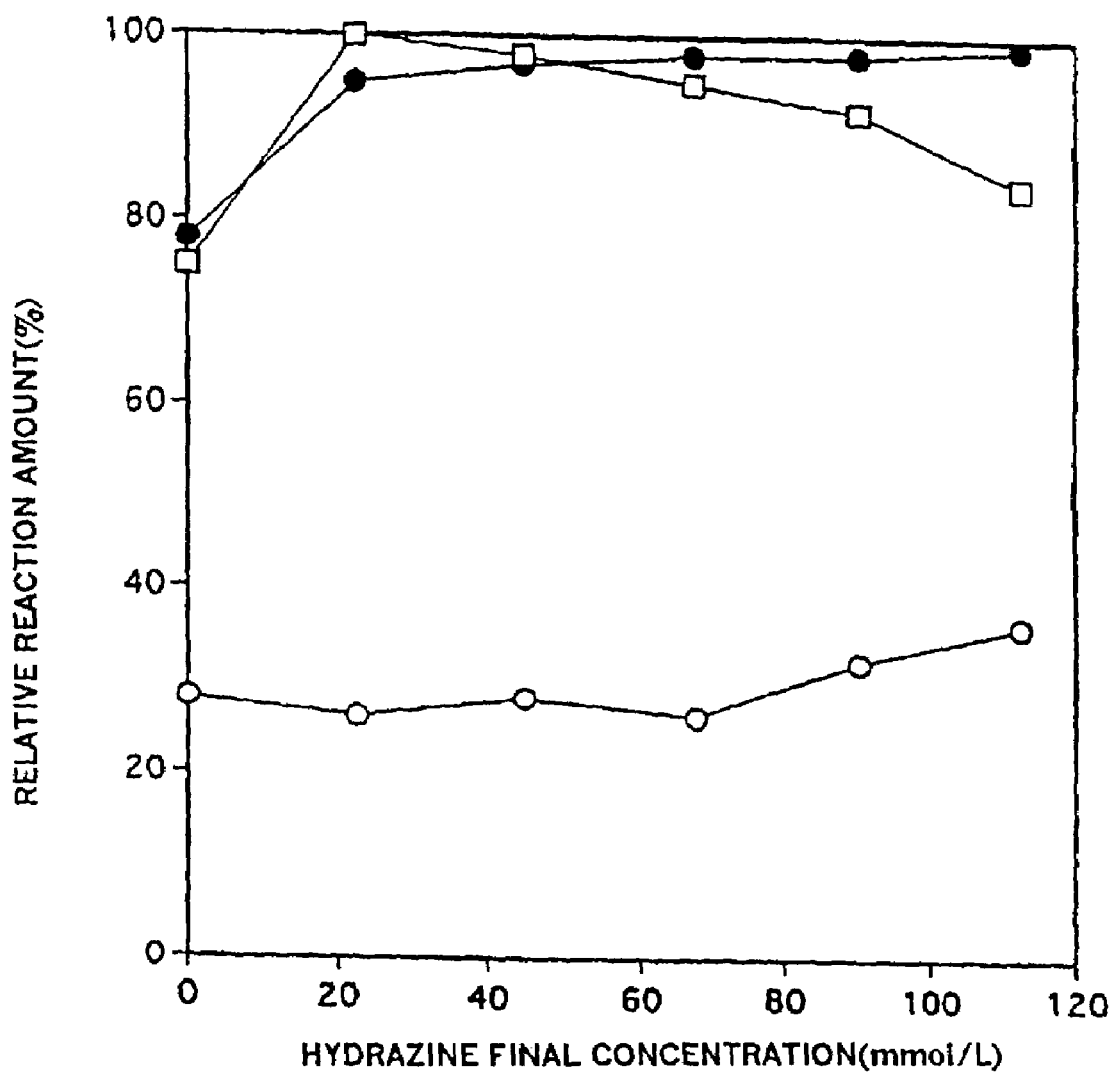
FIG. 2 is a diagram illustrating the effect of addition of hydrazine. (Experiment 2) In the figure, -●- indicates the relative reaction amount (%) of an HDL fraction, -○- indicates the relative reaction amount (%) of an LDL fraction, and -□- indicates the relative reaction amount (%) of a VLDL fraction.

Discussion on Experiment 2 (FIG. 2)

The effect of addition of hydrazine was confirmed. The addition of hydrazine further strengthened the specific reactivity of LPL with respect to the HDL fraction. The reactivity with respect to the LDL fraction showed substantially no variation. Based on the results, 100 mmol/L of hydrazine was added to reagent 1-D.

Figure 3:
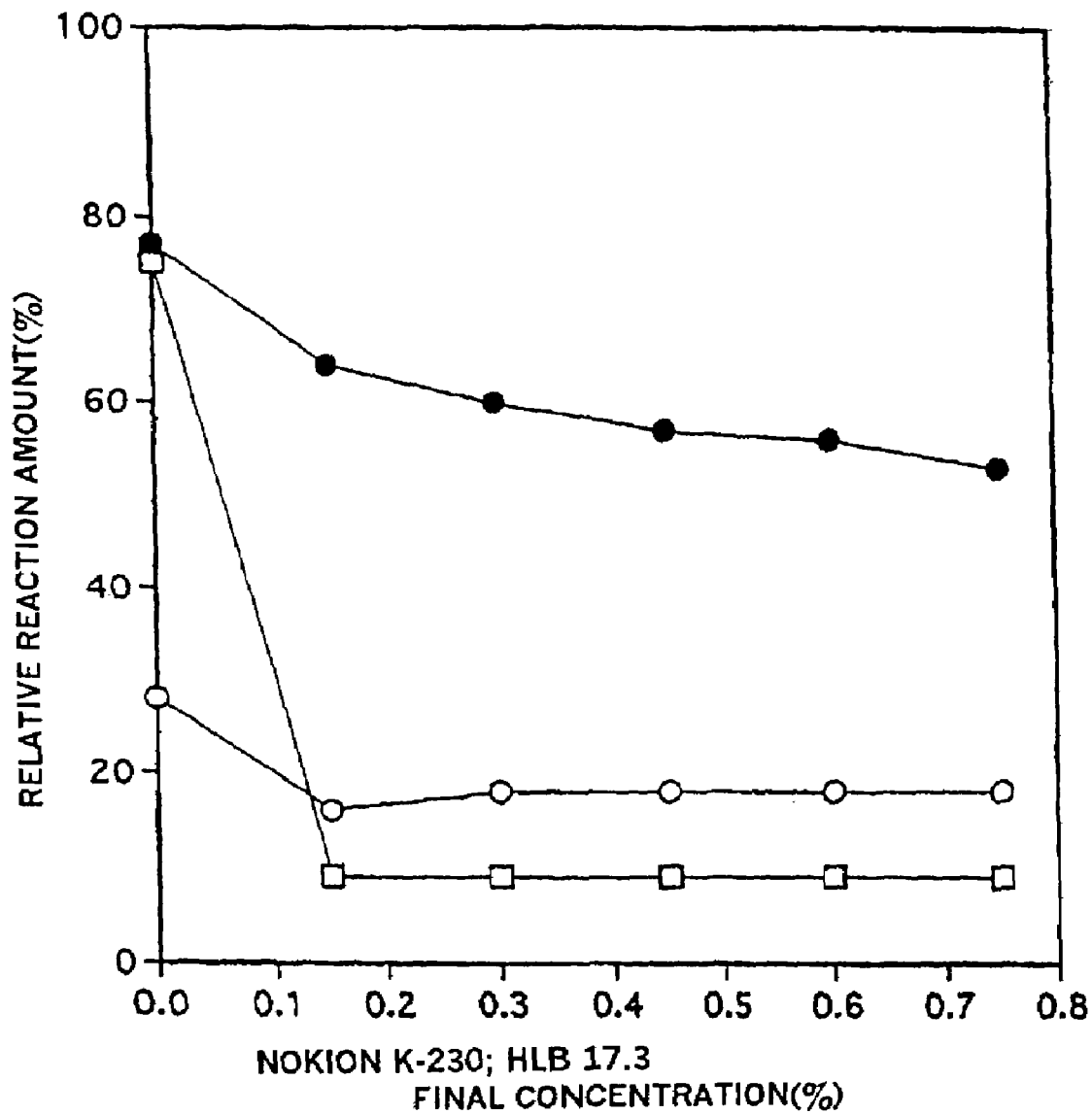
FIG. 3 is a diagram illustrating the effect of addition of a nonionic surfactant that has an HLB value of 17.3, Nonion K-230. (Experiment 3) In the figure, -●- indicates the relative reaction amount (%) of an HDL fraction, -○- indicates the relative reaction amount (%) of an LDL fraction, and -□- indicates the relative reaction amount (%) of a VLDL fraction.

Discussion on Experiment 3 (FIG. 3)

Using a nonionic surfactant having an HLB value of 17.3, Nonion K-230 (Nippon Oils & Fats Co., Ltd.), the effect of addition on the HDL fraction was confirmed. The addition of nonionic surfactant extremely decreased the reactivity of LPL with respect to the VLDL and further strengthened the specific reactivity thereof with respect to the HDL fraction. The effect for decreasing the reactivity of LPL with the LDL fraction was also confirmed. Based on the results 0.6% of Nonion K-230 was added to the reagent 1-D.

Discussion on Experiment 4 (FIG. 4)

As a result of applying the respective means, i.e., Nonion K-230, hydrazine and LPL in combination, a more perfect selective reaction system for the HDL fraction was established.

The invention claimed is:

1. Reagents for detecting a cholesterol in a high-density lipoprotein contained in a biological sample, comprising a first reagent and a second reagent, wherein said first reagent comprises an ion strength controlling substance and a nonionic surfactant that has an HLB value of 16 or more, and said second reagent comprises a first enzyme that reacts with the cholesterol in the high-density lipoprotein and a second enzyme comprising cholesterol dehydrogenase or cholesterol oxidase, or both.

2. The reagents of claim 1, wherein the ion strength controlling substance is hydrazine, hydrazine salt, hydrazine hydrate, hydrazine solvate, NaCl, urea, guanidine, or semicarbazide.

3. The reagents of claim 1, wherein the ion strength controlling substance is hydrazine.

4. The reagents of claim 3, wherein the first reagent comprises the hydrazine at a concentration of 30 mM or more.

5. The reagents of claim 1, wherein the nonionic surfactant has a HLB value of 17 or more.

6. The reagents of claim 1, wherein the first enzyme is lipoprotein lipase or cholesterol esterase.

7. The reagents of claim 1, wherein the second enzyme is cholesterol dehydrogenase, and
the first reagent comprises β-nicotinamide adenine dinucleotide of an oxide type, thionicotinamide adenine dinucleotide of an oxide type, β-nicotinanaide adenine dinucleotide phosphate of an oxide type or thionicotinamide adenine dinucleotide phosphate of an oxide type, or combinations thereof.

8. Reagents for detecting a cholesterol in a low-density lipoprotein contained in a biological sample, comprising a first reagent and a second reagent, wherein said first reagent comprises an ion strength controlling substance, a first nonionic surfactant which has an HLB value of 16 or more, a first enzyme reacting a cholesterol in a high-density lipoprotein and a second enzyme selected from cholesterol dehydrogenase or cholesterol oxidase, or both and the second reagent comprising a second nonionic surfactant which has an HLB value of 11 to 13.

9. The reagents of claim 8 wherein the second reagent comprises a third enzyme that reacts the cholesterol in the low-density lipoprotein.

10. The reagents of claim 9, wherein the third enzyme is lipoprotein lipase or cholesterol esterase.

11. The reagents of claim 8, wherein the ion strength controlling substance is hydrazine, hydrazine salt, hydrazine hydrate, hydrazine solvate, NaCl, urea, guanidine, or semicarbazide, or combinations thereof.

12. The reagents of claim 8, wherein the ion strength controlling substance is hydrazine.

13. The reagents of claim 12, wherein the first reagent comprises the hydrazine at a concentration of 30mM or more.

14. The reagents of claim 8, wherein the first nonionic surfactant has a HLB value of 17 or more.

15. The reagents of claim 8, wherein the first enzyme is lipoprotein lipase or cholesterol esterase, or both.

16. The reagents of claim 8, wherein the second enzyme is cholesterol dehydrogenase, and
the first reagent comprises β-nicotinantide adenine dinucleotide of an oxide type, thionicotinamide adenine dinucleotide of an oxide type, β-nicotinamide adenine dinucleotide phosphate of an oxide type, or thionicotinamide adenine dinucleotide phosphate of an oxide type, or combinations thereof.

17. A method of assaying cholesterol in a high-density lipoprotein fraction contained in a biological sample, comprising:
providing reagents for detecting a cholesterol in a high-density lipoprotein contained in a biological sample, comprising a first reagent and a second reagent, wherein said first reagent comprises an ion strength controlling substance and a nonionic surfactant that has an HLB value of 16 or more, and said second reanent comprises a first enzyme that reacts with the cholesterol in the high-density lipoprotein and a second enzyme comprising cholesterol dehydrogenase or cholesterol oxidase, or both; and utilizing the reagents to assay the high-density lipoprotein fraction, wherein utilizing the reagents to assay the high-density lipoprotein fraction comprises assaying the high-density lipoprotein fraction with said reagents, wherein said reagents are added to the sample and quantitating cholesterol generated by action of the first reagent and second reagent on the sample.

18. A method of assaying cholesterol in a low-density lipoprotein fraction contained in a biological sample, comprising:

providing reagents for detecting a cholesterol in a low-density lipoprotein contained in a biological sample, comprising a first reagent and a second reagent, wherein said first reagent comprises an ion strength controlling substance, a first nonionic surfactant which has an HLB value of 16 or more, a first enzyme reacting with a cholesterol in a high-density lipoprotein and a second enzyme selected from cholesterol dehydrogenase or cholesterol oxidase, or both and the second reagent comprising a second nonionic surfactant which has an HLB value of 11 to 13; and utilizing the reagents to assay the low-density lipoprotein fraction, wherein utilizing the reagents to assay the low-density lipoprotein fraction comprises assaying the low-density lipoprotein fraction with said reagents, wherein said reagents are added to the sample and quantitating cholesterol generated by action of the first reagent and second reagent on the sample.

19. Reagent combination for detecting a cholesterol in a high-density lipoprotein contained in a biological sample, comprising a first reagent and a second reagent, wherein said first reagent comprises an ion strength controlling substance and a nonionic surfactant that has an HLB value of 16 or more, and said second reagent comprises a first enzyme that reacts with the cholesterol in the high-density lipoprotein and a second enzyme comprising at least one of cholesterol dehydrogenase and cholesterol oxidase.

* * * * *

UNITED STATES PATENT AND TRADEMARK OFFICE
CERTIFICATE OF CORRECTION

PATENT NO. : 7,208,287 B2 Page 1 of 1
APPLICATION NO. : 10/776970
DATED : April 24, 2007
INVENTOR(S) : Kishi et al.

It is certified that error appears in the above-identified patent and that said Letters Patent is hereby corrected as shown below:

IN THE CLAIMS:

Claim 17, column 13, line 2, "reanent" should read --reagent--.

Signed and Sealed this

Twelfth Day of June, 2007

JON W. DUDAS
*Director of the United States Patent and Trademark Office*